United States Patent [19]

Ono et al.

[11] Patent Number: 5,789,606
[45] Date of Patent: Aug. 4, 1998

[54] EPOXIDIZING AGENT

[75] Inventors: Taizo Ono, Gifu; Haruhiko Fukaya, Aichi; Masakazu Nishida, Aichi; Takashi Abe, Aichi, all of Japan

[73] Assignee: Japan as represented by Director General of Agency of Industrial Science and Technology, Tokyo, Japan

[21] Appl. No.: 713,181

[22] Filed: Sep. 12, 1996

[30] Foreign Application Priority Data

Sep. 12, 1995 [JP] Japan ................................ 7-259235

[51] Int. Cl.$^6$ ........................................... C07D 301/03
[52] U.S. Cl. ............................................. 549/523
[58] Field of Search ............................................. 549/523

[56] References Cited

U.S. PATENT DOCUMENTS 3,358,003  12/1967  Eleuterio et al. .

FOREIGN PATENT DOCUMENTS 0100488  2/1984  European Pat. Off. .

OTHER PUBLICATIONS

"Hexafluoro–epoxy Propane Oligomer Preparation by Polymerizing Corresponding Monomer Over Catalyst in Presence of Organic Diluent Containing a Glycol" In–House Computer Generated Abstract (p. 46) of JP 78–123900—Oct. 6, 1978.
Battioni et al; Answer 2 of 24; 1996:588078; Doc. No. 125:276774 Chem. Commun. (Cambridge)(17); 2037–2038; 1996 Abstract pp. 6 and 7.
Inchley et al; Answer 5 of 24; 1995:742160. Doc. No. 123:227463 J. Chem. Soc., Perkin Trans. 2 (8) 1579–87, 1995 Abstract pp. 10 and 11.
Aihara et al; JP63027487 A2 880205 Answer 19 of 24 Doc. No. 110:8026 Abstract pp. 30 and 31.
I.P. Kolenko, T. I. Filyakova, A. Yazapevalov, and E. P. Lure, Izvest. Akad. Nauk. S.S.S. R., Ser. Khim., (1979), 2509.
Zh. Org. Khim., vol. 21, No. 10, 2113–2119 (1995).
Zh. Org. Khim., vol. 20, No. 11, 2267–2273 (1984).
SU–666176–A Abstract (1979).

*Primary Examiner*—Joseph L. Schofer
*Assistant Examiner*—N. Sarofim
*Attorney, Agent, or Firm*—Oblon, Spivak, McClelland, Maier & Neustadt, P.C.

[57] ABSTRACT

The object of the invention is to provide a novel process for epoxidation of perfluoro-olefins.

This invention relates to a process for epoxidizing a perfluoro-olefin, characterized by employing a tertiary amine N-oxide represented by the general formula (I):

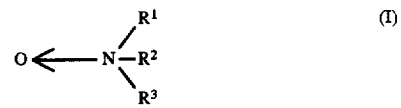

(wherein $R^1$, $R^2$ and $R^3$ each is a straight-chain or branched alkyl group having 1 to 10 carbon atoms, a lower alkyl group having 1 to 3 carbon atoms, or an aromatic group which may have a nitro group or a cyano group as a substituent; provided that all of $R^1$, $R^2$ and $R^3$ are selected from the above alkyl groups, $R^1$, $R^2$ and $R^3$ may combine with one another directly or through oxygen atoms or nitrogen atoms to form a cyclic compound of 5–7 membered ring), or iodosobenzene.

According to the present invention, perfluoro-olefins can be converted to corresponding perfluoroepoxides cheaply and in high yields. Epoxides produced by the process of this invention are utilized as intermediates for syntheses of surface active agents, lubricant oils, water repellents, oil repellents, polymers, and the like.

9 Claims, No Drawings

EPOXIDIZING AGENT

DESCRIPTION OF THE INVENTION

The present invention relates to a novel process for epoxidation of perfluoro-olefins, characterized by using a tertiary amine N-oxide such as trimethylamine-N-oxide or iodosobenzene as an oxidizing agent More specifically, the present invention relates to a process for epoxidizing a perfluoro-olefin, characterized by employing a tertiary amine N-oxide represented by the general formula:

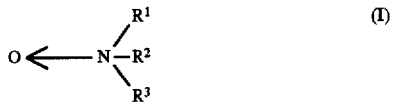

(wherein $R^1$, $R^2$ and $R^3$ each is a straight-chain or branched alkyl group having 1 to 10 carbon atoms, a lower alkyl group having 1 to 3 carbon atoms, or an aromatic group which may have a nitro group or a cyano group as a substituent; provided that all of $R^1$, $R^2$ and $R^3$ are selected from the above alkyl groups, $R^1$, $R^2$ and $R^3$ may combine with one another directly or through oxygen atoms or nitrogen atoms to form a cyclic compound of 5–7 membered ring), or iodosobenzene, and epoxidizing a perfluoro-olefin represented by the general formula:

(wherein $X_1$, $X_2$, $X_3$ and $X_4$ each is a substituent selected from (a) a fluorine atom, and (b) a straight-chain or branched perfluoroalkyl group having 1 to 5 carbon atoms). Epoxides prepared by the process of this invention are utilized as intermediates for syntheses of surface active agents, lubricant oils, water repellents, oil repellents, polymers, and the like.

BACKGROUND ART OF THE INVENTION

The epoxy-compounds of perfluoro-olefins have been synthesized by an epoxidation reaction of corresponding perfluoro-olefins. For examples, known processes include a process for converting a perfluoro-olefin to a corresponding perfluoroepoxide in a medium of an alkaline peroxide (U.S. Pat. No. 3,358,003), a process for epoxidizing a perfluoro-olefin in a system of an aqueous hypochlorite solution, wherein a polar solvent such as acetonitrile and diglyme was added (I. P. Kolenko, T. I. Filyakova, A. YaZapevalov, and E. P. Lure, Izvest. Akad. Nauk. S.S.S.R., Ser. Khim., (1979) 2509; U.S.S.R. Pat. 666,176 (1979)), and a process for epoxidizing a perfluoro-olefin in a system of an aqueous hypochlorite solution, wherein a phase transfer catalyst was added (Japanese Patent Publication No. 59-74285, Japanese Patent Publication No. 59-20277). Since all of the above processes employ an aqueous alkaline solution, it is difficult to prevent a resultant epoxide, which proceeded from a reaction with a hydroxide ion of the solution. Hence, the known processes have a defect that when the reaction time of it is lengthened to initiate the reaction, the yield of the epoxide is reduced. Hence, on purpose to reduce the influence of the hydroxide ion, a patent relating to an epoxidation of a perfluoro-olefin, characterized by dissolving the perfluoro-olefin in an organic solvent immiscible with water, and employing an aqueous hypochlorite solution in the presence of a phase transfer catalyst, is disclosed (EP 0100488); however, the yield of the epoxide is insufficiently from 30 to 40% in the case of a terminal olefin, and other Examples, which desclose no description about a yield of the epoxide, suggest a low yield of it. In addition, there is another problem that generally it is difficult to separate and purify a perfluoroepoxide formed from an organic solvent immiscible with water. In addition, a process for oxidation of a perfluoro-olefin with oxygen without employing alkaline conditions is known (Japanese Patent Publication No. 45-11683), however it employs such a solvent as 1,1,2-trichloro-1,2,2-trifluoroethane, and therefore it is difficult to prevent said problem upon separation and purification of the product, and further percentages of the conversion and the yield of the product are not sufficient.

SUMMARY OF THE INVENTION

This invention relates to a process for epoxidizing a perfluoro-olefin, characterized by employing a tertiary amine N-oxide represented by the general formula (I):

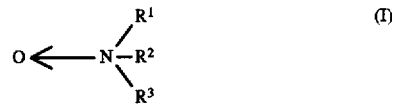

(wherein $R^1$, $R^2$ and $R^3$ each is a straight-chain or branched alkyl group having 1 to 10 carbon atoms, a lower alkyl group having 1 to 3 carbon atoms, or an aromatic group which may have a nitro group or a cyano group as a substituent; provided that all of $R^1$, $R^2$ and $R^3$ are selected from the above alkyl groups, $R^1$, $R^2$ and $R^3$ may combine with one another directly or through oxygen atoms or nitrogen atoms to form a cyclic compound of 5–7 membered ring), or iodosobenzene.

DETAILED DESCRIPTION OF THE INVENTION

Under these circumstances, the object of the present invention is to provide a process for epoxidation of perfluoro-olefins, by employing an easily available oxidizing agent, and epoxidizing the perfluoro-olefins in the presence of the oxidizing agent, under mild conditions and in high yields, and further by a simplified purification procedure.

The present inventor has engaged in assiduous studies with a view to accomplishing the above-mentioned object, and as a result, has found an epoxidation reaction of perfluoro-olefins by employing tertiary amine N-oxide or iodosobenzene as an oxidizing agent, under mild conditions and in high yields, and further by a simplified purification procedure, which has led to the accomplishment of the present invention.

That is, the present invention relates to provide a process for epoxidation of a perfluoro-olefin, characterized by employing a tertiary amine N-oxide represented by the general formula:

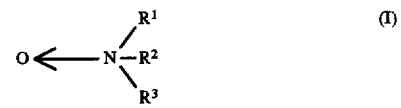

(wherein $R^1$, $R^2$ and $R^3$ each is a straight-chain or branched alkyl group having 1 to 10 carbon atoms, a lower alkyl group having 1 to 3 carbon atoms, or an aromatic group which may have a nitro group or a cyano group as a substituent; provided that all of $R^1$, $R^2$ and $R^3$ are selected from the above alkyl groups, $R^1$, $R^2$ and $R^3$ may combine with one another directly or through oxygen atoms or nitrogen atoms to form a cyclic compound of 5–7 membered ring), or iodosobenzene, and epoxidizing a perfluoro-olefin represented by the general formula:

(wherein $X_1$, $X_2$, $X_3$ and $X_4$ each is a substituent selected from (a) a fluorine atom, and (b) a straight-chain or branched perfluoroalkyl group having 1 to 5 carbon atoms).

Hereunder the present invention will be described in more detail.

As to the compounds represented by the above general formula (I) according to the present invention, the compounds other than commercially available trimethylamine-N-oxide dihydrate and N-methyl morpholine-N-oxide can be synthesized easily, by oxidizing a commercially available tertiary amine or a tertiary amine capable of being synthesized easily by a known method, according to a known process. For example, N,N-dimethylaniline-N-oxide used in Example 9 can be obtained by oxidizing N,-dimethylaniline with methachloroperbenzoic acid quantitatively. The compounds of the general formula (I) are not restricted to the three kinds of tertiary amine-N-oxides exemplified here, but trimethylamine-N-oxide is particularly preferable, since it is cheaply and easily available and exhibits a high yield.

A solvent to be used in an epoxidation reaction is selected from lower alcohols such as methanol, ethanol and isopropanol, non-proton polar solvents such as acetonitrile, dimethylformamide (DMF), dimethyl sulfoxide (DMSO), N-methyl pyrrolidone, hexamethyl phosphor amide (EMPA) and 1,3-dimethyl-2-imidazoline, other polar solvents such as acetone and diglyme, and water; and acetonitrile and DMF are preferable. The process for drying the solvents does not cause any problem; however, if a resultant perfluoroepoxide is unstable to water, a preferable result can be obtained by employing a solvent dried by an ordinary method, namely, a solvent dried with calcium hydride. Reaction temperature depends on the structure of a perfluoro-olefin to be epoxidized; generally the epoxidation is conducted at room temperature. In the case of a perfluoro-olefin having a high reactivity such as perfluoro-2-methyl-2-pentene, however, it is preferable to select a tertiary amine-N-oxide having a low reactivity, or to cool a reaction solvent and the perfluoro-olefin to such a degree as they are not solidified. For example, when DMF is employed as a reaction solvent, the reaction is performed at a temperature in the range of −60° to 0° C., preferably in the range of −40° to −5° C. The optimum temperature and combination of reagents can be found easily by an ordinary chemist according to a proper trial.

EXAMPLES

Hereunder the present invention will be described in more detail with reference to the examples; the present invention is not restricted to these examples.

Example 1

In a 25-ml flask with side arm equipped with a septum in which a stirrer coated with Teflon was incorporated were charged 3 ml of dimethylformaldehyde (DMF), and further trimethylamine-N-oxide dihydrate (450.7 mg, 4.06 mmols). To the obtained suspension was added perfluoro-3-isopropyl-4-methyl-2-propane thereinafter referred to as T-2) (1.26 g, 2.8 mmols, containing 8.1% of perfluoro-3-ethyl-2,4-dimethyl-2-propene isomer (hereinafter referred to as T-3)), and the stirrer in the reaction flask was rotated well at room temperature for 30 minutes. To the reaction solution was added 6 ml of water and the reaction mixture was settled, and the resultant lower layer separated was pipetted (1.25 g). It was confirmed by $^{19}$F-NMR that the this compound obtained corresponded to perfluoro-2,3-epoxy-3-isopropyl-4-methylpentane in comparison with the data described in the reference (Zh. Org. Khim., Vol. 21, No. 10, pp. 2113–2119, (1985)). Quantitative assay of the resultant product by gas chromatography showed that the purity of the product was 98%.

Example 2

In a 25-ml flask with a side arm equipped with a septum and a water-cooling cold finger in which a stirrer coated with Teflon was incorporated was charged powdered trimethylamine-N-oxide dehydrate (900 mg, 8.1 mmols) pulverized well in a mortar. To the reaction flask was added T-2 (1.26 g, 2.8 mmols, containing 8.1% of T-3), and the stirrer in the reaction flask was rotated for 3 days to mix the reaction solution, wherein the flask was placed in an oil bath heated to 60° C. The reaction solution was settled at room temperature, and to the reaction solution was added 10 ml of water, and the resultant lower layer separated was pipetted (1.2 g). Quantitative assay of the resultant product by gas chromatography showed that the product contained 8.1% of T-3 and 80.6% of the aimed epoxide.

Example 3

In a 25-ml flask with a side arm equipped with a septum in which a stirrer coated with Teflon was incorporated were charged 3 ml of dimethylformaldehyde (DMF), and further trimethylamine-N-oxide dehydrate (450.7 mg, 4.06 mmols). To the obtained suspension was added T-3 (1.26 g 2.8 mmols), and the stirrer in the reaction flask was rotated to mix the reaction solution at room temperature for one hour. To the reaction solution was added 10 ml of water and the solution was settled, and the resultant lower layer separated was pipetted (1.25 g). Quantitative assay of the resultant product by gas chromatography showed that the purity of the product was 97%.

Example 4

In a 25-ml flask with a side arm equipped with a Jimroth condenser was incorporated a stirrer coated with Teflon, and a septum was installed in the side arm of the flask. To the reaction flask were added T-2 (1.26 g, 2.8 mmols, containing 8.1% of T-3) and a 50% aqueous morpholine-N-oxide solution, and the stirrer in the reaction flask was rotated to mix the reaction solution for 2 days, wherein the flask was heated in an oil bath heated to 110° C. The reaction solution was settled at room temperature, and to the reaction solution was added 6 ml of water and the solution was settled, and the resultant lower layer separated was pipetted (1.1 g). Quantitative assay of the resultant product by gas chromatography showed that the product contained 25% of the aimed epoxide, and the rests of it were T-2 and T-3 of starting raw materials.

Example 5

In a 30-ml flask with a side arm equipped with a septum in which a stirrer coated with Teflon was incorporated were charged trimethylamine-N-oxide dihydrate (444 mg, 4 mmols), benzene (15 ml) and further methanol (2 ml). After dried for 5 hours by azeotropic distillation using a Dean-Stark tube, the solvents were removed under vacuum. To the white powder obtained was added 5 ml of dried DMF. To the reaction flask was added perfluoro-2-methyl-2-pentene (0.9 g, 3 mmols) with an injector through the septum, wherein the stirrer in the reaction flask was rotated to mix the reaction solution, and the reaction flask was placed in an isopanol bath adjusted to −40° C. Besides, after the stirrer was rotated at the same temperature for 70 minutes, the solution was settled, and the lower layer separated was pipetted (0.77 g). It was confirmed by $^{19}$F-NMR that the thus obtained compound corresponded to perfluoro-2,3-epoxy-2-methylpentane in comparison with the data described in the reference (Izvest. Akad. Nauk. S.S.S.R., Ser. Khim., pp. 2509–2513, (1979)). Quantitative assay of the resultant product by gas chromatography showed that the purity of the product was 100%.

Example 6

In a 25-ml flask with a side arm equipped with a septum in which a stirrer coated with Teflon was incorporated were charged 3 ml of dimethylformaldehyde (DMF), and further trimethylamine-N-oxide dihydrate (911 mg, 8.2 mmols). To the obtained suspension was added perfluoro-2,4-dimethyl-3-pentene (referred to as T-1) (2.3 g, 4.66 mmols, containing 2.8% of T-2 and 6.0% of T-3), and the stirrer in the reaction flask was rotated to mix the reaction solution at room temperature for 2 hours, till T-1 as the raw material was not detected by gas chromatography. To the reaction solution were added 10 ml of water and the solution was settled, and the resultant lower layer separated was pipetted (1.58 g). Quantitative assay of the resultant product by gas chromatography showed that it contained 58% of epoxide. As to the structure of the thus obtained compound, it was confirmed by $^{19}$F-NMR using a sample purified by gas chromatography that the compound corresponded to perfluoro-3,4-epoxy-2,4-dimethylheptane in comparison with the data described in the reference (Zh. Org. Khim., Vol. 20, No. 11, pp. 2267–2273, (1984))

Example 7

In a 25-ml flask with a side arm equipped with a septum in which a stirrer coated with Teflon was incorporated were charged 2 ml of dimethylformaldehyde (DMF), methachloroperbenzoic acid (711.9 mg, 3.3 mmols) with a purity of 80%, and 50 μl of a 40% aqueous trimethylamine solution, and the stirrer in the reaction flask was rotated to mix the reaction solution. To the obtained reaction solution was added T-2 (1.35 g, 3 mmols, containing 12.4% of T-3), and the stirrer was rotated to mix the reaction solution at room temperature for 30 minutes. The lower layer separated was pipetted and filtered through a glass-wool filter to obtain 1.37 g of a reaction mixture. Quantitative assay of the reaction mixture by gas chromatography showed that it contained 14.5% of T-2, 10.7% of T-3 and 74.7% of the epoxide.

Example 8

The reaction was performed in a manner similar to Example 7 except that 4.5 mmols of methachloroperbenzoic acid was used, and reaction time was changed to one hour, to obtain 1.34 g of a resultant product. Quantitative assay of the product by gas chromatography showed that it contained 86.1% of the epoxide.

Example 9

In a 25-ml flask with a side arm equipped with a septum in which a stirrer coated with Teflon was incorporated was charged N,N-dimethylaniline-N-oxide (356.2 mg, 2.6 mmols) dissolved in 2 ml of acetonitrile.

In the reaction flask was added perfluoro-2-methyl-2-pentene (0.6 g, 2 mmols), wherein the stirrer in the reaction flask was rotated to mix the mixture, and the rotation of the stirrer was continued at the same temperature for 20 minutes, and the reaction flask was placed in an isopropanol bath adjusted to −5° C. The reaction mixture was settled and the resultant lower layer separated was pipetted (0.38 g). Quantitative assay of the resultant product by gas chromatography showed that the conversion to the epoxide was 100% and the product contained 75.8% of the epoxide.

Example 10

In a 25-ml flask with a side arm equipped with a septum in which a stirrer coated with Teflon was incorporated were charged 2 ml of dimethylformaldehyde (DMF), and further iodobenzene (220 mg, 1 mmol) and T-2 (900 mg, 2 mmol, containing 8.1% of T-3), and the stirrer in the reaction flask was rotated to mix the reaction solution at room temperature for 32 hours. The lower layer separated was pipetted and filtered through a glass-wool filter to obtain 0.795 g of a reaction resultant product. Quantitative assay of the product by gas chromatography showed that it contained 42.7% of T-2, 12.3% of T-3 and 31.9% of the epoxide.

What is claimed is:

1. A process for epoxidizing a perfluoro-olefin, comprising oxidizing a perfluoro-olefin of general formula (II)

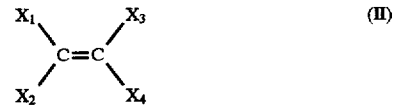

(wherein $X_1$, $X_2$, $X_3$ and $X_4$ each is a substituent selected from the group of (a) a fluorine atom, and (b) a straight-chain or branched perfluoroalkyl group having 1 to 5 carbon atoms)

with an oxidizing agent selected from the group consisting of (1) a tertiary amine N-oxide represented by the general formula (I):

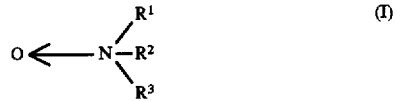

(wherein $R^1$, $R^2$ and $R^3$ each is a straight-chain or branched alkyl group having 1 to 10 carbon atoms, a lower alkyl group having 1 to 3 carbon atoms, or an aromatic group which may have a nitro group or a cyano group as a substituent; provided that all of $R^1$, $R^2$ and $R^3$ are selected from the above alkyl groups, $R^1$, $R^2$ and $R^3$ may combine with one another directly or through oxygen atoms or nitrogen atoms to form a cyclic compound of 5–7 membered ring) and (2) iodosobenzene, in the absence of a solvent or in the presence of a proper solvent under mild conditions.

2. The process of claim 1, wherein the tertiary amine oxide is formed by oxidizing a tertiary amine.

3. The process of claim 1, wherein the oxidizing agent is trimethylamine-N-oxide.

4. The process of claim 1, wherein the oxidizing agent is N-methylmorpholine-N-oxide.

5. The process of claim 1, wherein the oxidizing agent is morpholine-N-oxide.

6. The process of claim 1, wherein the oxidizing agent is iodobenzene.

7. The process of claim 2, wherein the tertiary amine is trimethylamine.

8. The process of claim 1, conducted in the absence of any substantial amount of another oxidizing agent.

9. The process of claim 1, conducted in the absence of any amount of another oxidizing agent.

* * * * *